United States Patent
Shimizu

(10) Patent No.: US 9,950,980 B2
(45) Date of Patent: Apr. 24, 2018

(54) FLUOROPOLYETHER COMPOUND, LUBRICANT CONTAINING SAME, AND MAGNETIC DISK

(71) Applicant: MORESCO CORPORATION, Kobe-shi, Hyogo (JP)

(72) Inventor: Tsuyoshi Shimizu, Kobe (JP)

(73) Assignee: Moresco Corporation, Kobe-shi, Hyogo (JP)

( * ) Notice: Subject to any disclaimer, the term of this patent is extended or adjusted under 35 U.S.C. 154(b) by 244 days.

(21) Appl. No.: 14/913,012

(22) PCT Filed: Nov. 25, 2014

(86) PCT No.: PCT/JP2014/081072
§ 371 (c)(1),
(2) Date: Feb. 19, 2016

(87) PCT Pub. No.: WO2015/093237
PCT Pub. Date: Jun. 25, 2015

(65) Prior Publication Data
US 2016/0203839 A1    Jul. 14, 2016

(30) Foreign Application Priority Data
Dec. 17, 2013  (JP) .................. 2013-260353

(51) Int. Cl.
  *G11B 5/725*  (2006.01)
  *C07C 43/23*  (2006.01)
  (Continued)

(52) U.S. Cl.
  CPC ............ *C07C 43/23* (2013.01); *C07C 43/137* (2013.01); *C07C 43/225* (2013.01);
  (Continued)

(58) Field of Classification Search
  CPC ....... G11B 5/732; C07C 43/20; C07C 43/205; C07C 43/2055; C07C 43/225;
  (Continued)

(56) References Cited

U.S. PATENT DOCUMENTS

2006/0068998 A1  3/2006  Negoro et al.
2010/0028721 A1  2/2010  Hamakubo et al.
(Continued)

FOREIGN PATENT DOCUMENTS

JP  2006-070173      3/2006
JP  2006-117928 A    5/2006
(Continued)

OTHER PUBLICATIONS

Machine translation of JP 2009/270093, Japan, pp. 1-15.Nov. 2009.*

*Primary Examiner* — Holly Rickman
(74) *Attorney, Agent, or Firm* — Morgan, Lewis & Bockius LLP

(57) ABSTRACT

An object of the present invention is to provide a compound that is resistant to decomposition even when coming into contact with a magnetic head, while enabling a reduced spacing between the magnetic head and a magnetic disk, and to provide a lubricant comprising the compound, and a magnetic disk comprising the compound. The present invention relates to a compound represented by formula (1), a lubricant comprising the compound, and a magnetic disk comprising the compound:

$$C_6H_{6-i}-[O-(CH_2)_n-O-CH_2-R-CH_2-X]_i \qquad (1)$$

wherein n is an integer of 2 to 6; i is an integer of 2 or 3; X is a group represented by $-OH$, $-O-(CH_2)_m-OH$, $-OCH_2CH(OH)CH_2OH$, $-OCH_2CH(OH)CH_2O-C_6H_5$, or $-OCH_2CH(OH)CH_2O-C_6H_4-OCH_3$; m is an integer of 1 to 6; R is $-(CF_2)_pO(CF_2O)_x(CF_2CF_2O)_y$ (Continued)

$-(CF_2CF_2CF_2O)_z(CF_2CF_2CF_2CF_2O)_w(CF_2)_p-$; x and y are each a real number of 0 to 30; z is a real number of 0 to 30; w is a real number of 0 to 20; and p is an integer of 1 to 3.

3 Claims, 1 Drawing Sheet

(51) Int. Cl.
    *C07C 43/13* (2006.01)
    *C07C 43/225* (2006.01)
    *C10M 105/54* (2006.01)
    *C10M 107/38* (2006.01)

(52) U.S. Cl.
    CPC ........ *C10M 105/54* (2013.01); *C10M 107/38* (2013.01); *G11B 5/725* (2013.01); *C10M 2211/0425* (2013.01); *C10M 2213/043* (2013.01); *C10N 2230/06* (2013.01); *C10N 2240/204* (2013.01)

(58) Field of Classification Search
    CPC ........... C07C 43/137; C10M 2213/043; C10M 2211/0425; C10M 107/38; C10M 105/54; C10N 2230/06; C10N 2240/204
    See application file for complete search history.

(56) References Cited

U.S. PATENT DOCUMENTS

| | | | |
|---|---|---|---|
| 2010/0197869 A1 | 8/2010 | Tonelli | |
| 2012/0219826 A1* | 8/2012 | Li | C07C 43/1786 428/800 |
| 2012/0315504 A1* | 12/2012 | Shimizu | C07C 43/23 428/800 |

FOREIGN PATENT DOCUMENTS

| | | |
|---|---|---|
| JP | 2009-270093 A | 11/2009 |
| JP | 2013-018961 A | 1/2013 |
| JP | 5327855 B2 | 8/2013 |
| WO | 2008/038799 A1 | 4/2008 |

\* cited by examiner

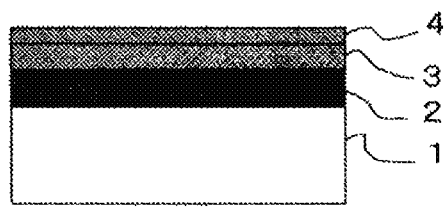

FLUOROPOLYETHER COMPOUND, LUBRICANT CONTAINING SAME, AND MAGNETIC DISK

TECHNICAL FIELD

The present invention relates to a fluoropolyether compound having an aromatic group and hydroxyl groups, a lubricant containing the compound and a magnetic disk having the lubricant applied thereto.

BACKGROUND ART

With the increased recording density of magnetic disks, the distance between a magnetic disk serving as a recording medium and a head for recording and reproducing information has become almost nil as they approach coming into contact with each other. The magnetic disk surface is provided with a carbon protective film and a lubricant film to diminish abrasion caused by contact with the head or sliding of the head thereon, and to prevent contamination of the disk surface. The carbon protective film is typically formed by sputtering or CVD. The disk surface is protected by two films, i.e., the carbon protective film and the lubricant film provided thereover. In particular, the lubricant layer provided on the top must have various properties, such as long-term stability, chemical resistance, friction properties, and heat resistance.

Conventionally used lubricants for magnetic disks are fluoropolyethers having functional groups, such as hydroxyl and amino, at their molecular terminals. However, fluoropolyether-based lubricants have low durability against Lewis acids. When the lubricants come into contact with the magnetic head, their backbone is cleaved by alumina ($Al_2O_3$; contained in a magnetic head component, whereby the lubricants become lower molecules, ultimately dissipating from the magnetic disk surface. Thus, the film formed by such lubricants cannot be maintained in a system where the magnetic head comes into contact with the magnetic disk or slides on the magnetic disk, A recent rapid increase in the information recording density of magnetic disks requires a reduction in magnetic spacing between the magnetic head and the recording layer of the magnetic disk. It is thus becoming important to further reduce the thickness of the lubricant layer present between the magnetic head and the recording layer of the magnetic disk.

In response to this need, fluoropolyether-based lubricants have been proposed which have functional groups at their molecular terminals and in the middle of the molecular chains (e.g., Patent Documents 1 to 4). Patent Document 1 teaches that the use of a lubricant having hydroxyl both in the molecular chain and at the molecular terminals reduces the thickness of one molecule even when the lubricant is highly polymerized. Patent Document 2 teaches that the use of a lubricant having hydroxyl at the molecular terminals and in the center of the molecular chain, optionally with an aromatic ring in the center of the molecular chain, reduces the thickness of a lubricant layer while enabling high film coverage. Patent Document 3 teaches that the use of a compound having an aromatic ring at the molecular terminals and in the center of the molecular chain can improve the heat resistance. Patent Document 4 teaches that the use of a lubricant having hydroxyl at the molecular terminals and a benzene ring in the center of the molecular chain reduces the thickness of one molecule to thereby reduce the spacing between the head and the disk, thus enabling durability against sliding.

However, neither of Patent Documents 1 to 4 discloses a lubricant that can reduce the thickness of one molecule to thereby reduce the spacing between the magnetic head and the magnetic disk, while being resistant to decomposition by alumina when coming into contact with the magnetic head.

CITATION LIST

Patent Documents

Patent Document 1: JP2006-070173A
Patent Document 2: International Publication No. WO2008/038799
Patent Document 3: US2010/0197669A
Patent Document 4: Japanese Patent No. 5327855

SUMMARY OF INVENTION

Technical Problem

An object of the present invention is to provide a compound that is resistant to decomposition even when coming into contact with a magnetic head while enabling a reduced spacing between the magnetic head and the magnetic disk, and to provide a lubricant comprising the compound, and a magnetic disk comprising the compound.

Solution to Problem

The present inventor conducted extensive research, and found that the above-described object is achieved by the use of a compound having a benzene ring disubstituted or trisubstituted with a specific fluoropolyether chain having a functional group, such as hydroxyl, in the molecular terminal. The inventor then completed the present invention.

The present invention relates to the following compound, lubricant, and magnetic disk.

1. A compound represented by formula (1):

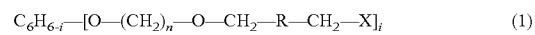

$$C_6H_{6-i}\text{—}[O\text{—}(CH_2)_n\text{—}O\text{—}CH_2\text{—}R\text{—}CH_2\text{—}X]_i \quad (1)$$

wherein n is an integer of 2 to 6; i is an integer of 2 or 3; X is a group represented by —OH, —O—$(CH_2)_m$—OH, —OCH$_2$CH(OH)CH$_2$OH, —OCH$_2$CH(OH)CH$_2$O—$C_6H_5$, or —OCH$_2$CH(OH)CH$_2$O—$C_6H_4$—OCH$_2$; m is an integer of 1 to 6; R is —$(CF_2)_p$O$(CF_2O)_x(CF_2CF_2O)_y$$(CF_2CF_2CF_2O)_z(CF_2CF_2CF_2CF_2O)_w(CF_2)_p$; x and y are each a real number of 0 to 30; z is a real number of 0 to 30; w is a real number of 0 to 20; and p is an integer of 1 to 3.

2. A lubricant comprising the compound represented by formula (1).

3. A magnetic disk comprising, in sequence, a substrate, a recording layer, and a protective layer, the magnetic disk further comprising a lubricant layer formed on the protective layer, the lubricant layer comprising the compound represented by formula (1).

Advantageous Effects of Invention

A fluoropolyether compound having an aromatic group and hydroxyl groups according to the present invention is a compound that can simultaneously achieve two objects, a reduction in thickness of one molecule and resistance to decomposition. A magnetic disk comprising a lubricant containing the compound according to the present invention enables reduced spacing between a magnetic head and a magnetic disk, and exhibits excellent durability when the head comes into contact with or slidably moves on the disk.

BRIEF DESCRIPTION OF DRAWINGS

FIG. 1 is a cross-sectional diagram showing the configuration of a magnetic disk according to the present invention.

DESCRIPTION OF EMBODIMENTS

The fluoropolyether represented by formula (1) according to the present invention is a fluoropolyether compound having an aromatic group and hydroxyl groups.

The compound represented by formula (1) according to the present invention can be obtained, for example, by reacting (a) a straight-chain fluoropolyether having a hydroxyl group at one terminal and an ester group, a siloxy group, or an alkoxy group at the other terminal with (b) benzene having 2 or 3 halogenated alkoxy groups. Specifically, the compound can be synthesized by the following process.

The first step is to synthesize (a) the straight-chain fluoropolyether having a hydroxyl group at one terminal and an ester group, a siloxy group, or an alkoxy group at the other terminal.

(c) A straight-chain fluoropolyether having a hydroxyl group at each terminal is reacted with (d) a compound that is reactive with a hydroxyl group to thereby produce an ester group, a siloxy group, or an alkoxy group. The reaction temperature is typically 10 to 60° C., and preferably 20 to 40° C. The reaction time is typically 2 to 20 hours, and preferably 10 to 15 hours. The compound (d) is added preferably in an amount of 0.5 to 1.5 equivalents based on the amount of the fluoropolyether (c). For this reaction, a reaction accelerator may be used. Thereafter, the reaction mixture is purified by, for example, column chromatography, to thereby obtain the straight-chain fluoropolyether having a hydroxyl group at one terminal and an ester group, a siloxy group, or an alkoxy group at the other terminal. The reaction may be carried out in a solvent. Examples of solvents include dimethylformaldehyde, 1,4-dioxane, dimethyl sulfoxide, and dimethylacetamide. Examples of reaction accelerators include imidazole, pyridine, and sodium hydroxide.

Examples of (c) fluoropolyethers having a hydroxyl group at each terminal include compounds represented by $HOCH_2CF_2CF_2CF_2O(CF_2CF_2CF_2CF_2O)_wCF_2CF_2CF_2CH_2OH$ (c-1), compounds represented by $HOCH_2CF_2O(CF_2O)_x(CF_2CF_2O)_yCF_2CH_2OH$ (c-2) and compounds represented by $HOCH_2CF_2CF_2O(CF_2CF_2CF_2O)_zCF_2CF_2CH_2OH$ (c-3) These fluoropolyethers have a number average molecular weight of typically 300 to 2,000, preferably 400 to 1,500, and more preferably 500 to 800. As used herein, the term "number average molecular weight" refers to a value of $^{19}F$-NMR measured with JNM-ECX400 (JEOL Ltd.). In NMR measurement, the samples themselves were measured without being diluted with a solvent. The standard chemical shift that was used is a known peak, which is a portion of the backbone structure of a fluoropolyether.

w is typically a real number of 0 to 20, preferably 0 to 10, and more preferably 0 to 5. x is typically a real number of 0 to 30, preferably 1 to 20, and more preferably 5 to 10. y is typically a real number of 0 to 30, preferably 1 to 20, and more preferably 5 to 10. z is typically a real number of 0 to 20, preferably 1 to 15, and more preferably 3 to 10. In Compound (c-1), p is 3; in Compound (c-2), p is 1; and in Compound (c-3), p is 2.

The fluoropolyether (c) is a compound having a molecular weight distribution. The molecular weight distribution (PD), which is represented by weight average molecular weight/number average molecular weight, is typically 1.0 to 1.5, preferably 1.0 to 1.3, and more preferably 1.0 to 1.1. The molecular weight distribution is a characteristic value obtained by using HPLC-8220GPC (Tosoh Corporation), a column (PLgel Mixed E; Polymer Laboratories Ltd.), an HCFC-based alternative CFC as an eluent, and a non-functional fluoropolyether serving as a reference material.

Examples of compounds that are reactive with a hydroxyl group to thereby produce an ester group, a siloxy group, or an alkoxy group include acid anhydrides, silyl halides, and alkyl halides.

Examples of acid anhydrides include maleic anhydride, succinic anhydride, phthalic anhydride, and compounds represented by $R^aOR^b$ wherein $R^a$ and $R^b$ are the same or different, and $R^a$ and $R^b$ are each $CH_3CO$, PhCO, $CR_3SO_2$, $PhSO_2$, $CF_3CH_2CO$, or $CH_3C_6H_4SO_2$ wherein Ph is phenyl. Specific examples of the compounds represented by $R^aOR^b$ include trifluoromethylacetic anhydride, benzoic anhydride, p-toluenesulfonic anhydride, trifluoromethanesulfonic anhydride, acetic anhydride, acetic benzoic anhydride, methanesulfonic anhydride, and benzenesulfonic anhydride.

Examples of silyl halides include $(R^c)_3SiY$, $R^d(R^e)_2SiY$, and $R^dR^eR^gSiY$ wherein $R^c$ is $C_{1-4}$ alkyl or Ph; $R^d$ is $C_{1-18}$ alkyl, $C_{1-4}$ alkoxy, Ph, $PhCH_2$, pentafluorophenyl, cyanopropyl, or vinyl; $R^e$ is $C_{1-2}$ alkyl or Ph; $P^g$ is $C_{1-4}$ alkyl substituted with phenyl; and Y is a halogen, such as chlorine, bromine, and iodine. Specific examples include trimethylsilyl chloride, triethylsilyl chloride, triisopropylsilyl chloride, t-butyldimethylsilyl chloride, butyldiphenylsilyl chloride, (3-cyanopropyl)dimethylchlorosilane, benzylchlorodimethylsilane, butyldimethylchlorosilane, chloro(decyl)dimethylsilane, chloro(dodecyl)dimethylsilane, chlorodimethyl(3-phenylpropyl)silane, chlorodimethylphenylsilane, chlorodimethylpropylsilane, chlorodimethylvinylsilane, diethylisopropylsilyl chloride, dimethyl-n-octylchlorosilane, dimethylethylsilyl chloride, dimethylisopropylchlorosilane, dimethyloctadecylchlorosilane, diphenylmethylchlorosilane, methyloctadecyl(3-phenylpropyl)chlorosilane, pentafluorophenyl dimethylchlorosilane, t-butoxydiphenylchlorosilane, t-butyldiphenylchlorosilane, and triphenylchlorosilane.

Examples of alkyl halides include compounds represented by AY wherein A is $C_{1-5}$ alkyl, and Y is a halogen, such as chlorine, bromine, and iodine. Specific examples include chloromethane, bromomethane, iodomethane, chloroethane, bromoethane, iodoethane, 1-bromopropane, 2-bromopropane, 1-iodopropane, 2-iodopropane, 1-bromo-2-methylpropane, 1-bromobutane, 2-bromo-2-methylpropane, 2-bromobutane, 1-iodo-2-methylpropane, 1-iodobutane, 2-iodo-2-methylpropane, 2-iodobutane, 1-iodo-2-methylbutane, 1-iodo-3-methylbutane, 1-bromo-3-methylbutane, 1-bromopentane, 2-bromo-2-methylbutane, and 3-bromopentane.

For example, when $HOCH_2CF_2CF_2CF_2O(CF_2CF_2CF_2CF_2O)_wCF_2CF_2CF_2CH_2OH$ and acetic anhydride are used, respectively, as Compound (c) and Compound (d), the reaction between these compounds generates $CH_3COOCH_2CF_2CF_2CF_2O(CF_2CF_2CF_2CF_2O)_wCF_2CF_2CF_2CH_2OH$, $CH_3COOH$, and $CH_3COOH$. The former is Compound (a). The use of trimethylsilyl chloride as Compound (d) generates $(CH_3)_3SiOCH_2CF_2CF_2CF_2O(CF_2CF_2CF_2CF_2O)_wCF_2CF_2CF_2CH_2OH$.

The second step is to synthesize the compound according to the present invention.

The fluoropolyether (a) obtained in the first step is reacted with benzene having 2 or 3 halogenated alkoxy groups (b) represented by formula (2)

  (2)

wherein n is an integer of 2 to 6; i is an integer of 2 or 3; and Y is a halogen, such as chlorine, bromine, and iodine, in the presence of a catalyst or an alkali metal.

In formula (2), n is preferably an integer of 2 to 4. Specific examples of compounds represented by formula (2) wherein i is 3 include 1,3,5-tri(bromopropoxy)benzene, 1,2,3-tri(bromopropoxy)benzene, 1,2,4-tri(bromopropoxy)benzene, 1,3,5-tri(bromoethoxy)benzene, 1,2,3-tri(bromoethoxy)benzene, and 1,2,4-tri(bromoethoxy)benzene. Specific examples of compounds represented by formula (2) wherein i is 2 include o-di(bromopropoxy)benzene, m-di(bromopropoxy)benzene, p-di(bromopropoxy)benzene, o-di(bromoethoxy)benzene, m-di(bromoethoxy)benzene, and p-di(bromoethoxy)benzene.

The reaction temperature is typically 50 to 100° C., and preferably 70 to 90° C. The reaction time is typically 20 to 100 hours, and preferably 50 to 80 hours. Compound (b) is preferably added in an amount of 0.2 to 1.0 equivalents based on the amount of Compound (a). The catalyst is preferably added in an amount of 0.05 to 0.1 equivalents based on the amount of Compound (a), and the alkali metal is preferably added in an amount of 1.0 to 2.0 equivalents based on the amount of Compound (a). Examples of catalysts for use include alkali compounds, such as sodium t-butoxide, potassium t-butoxide, and sodium, hydride. Examples of alkali metals for use include sodium and potassium. The reaction may be carried out in a solvent. Examples of solvents for use include t-butanol, toluene, and xylene. Thereafter, the reaction mixture is, for example, washed with water and dehydrated. Subsequently, the protecting group (an ester group, a siloxy group, or an alkoxy group) remaining at one terminal of the fluoropolyether is eliminated by hydrolysis or the like, thereby giving Compound (1) according to the present invention wherein X is —OH. For elimination of the protecting group, a deprotection promoter, such as tetrabutylammonium fluoride, potassium fluoride, and sodium fluoride, may be used.

Compound (1) according to the present invention wherein X is —O(CH$_2$)$_m$OH, —OCH$_2$CH(OH)CH$_2$OH, —OCH$_2$CH(OH)CH$_2$O—C$_6$H$_5$, or —OCH$_2$CH(OH)CH$_2$O—C$_6$H$_4$—CCH$_3$ can be produced from the compound wherein X is —OH obtained in the above-step in accordance with the following procedure, for example.

A reaction of the compound wherein X is —OH with a haloalcohol represented by Y(CH$_2$)$_m$OH wherein Y is a halogen, such as chlorine, bromine, and iodine, and m is an integer of 1 to 6 in the presence of an alkali metal generates Compound (11) according to the present invention wherein X is —O(CH$_2$)$_m$OH. m is preferably 1 to 4, and more preferably 2 to 4. Examples of alkali metals for use include sodium and potassium.

Compound (1) of the present invention wherein X is —CCH$_2$CH(OH)CH$_2$OH is obtained by reacting the compound wherein X is —OH with glycidol in the presence of a catalyst.

Compound (1) of the present invention wherein X is —OCH$_2$CH(OH)CH$_2$O—C$_6$H$_5$ is obtained by reacting the compound wherein X is —OH with glycidyl phenyl ether in the presence of a catalyst.

Compound (1) of the present invention wherein X is —OCH$_2$CH(OH)CH$_2$O—C$_6$H$_4$—OCH$_3$ is obtained by reacting the compound wherein X is —OH with glycidyl 4-methoxy phenyl ether in the presence of a catalyst.

The reaction temperature for these reactions is typically 50 to 100° C., and preferably 70 to 90° C. The reaction time is typically 20 to 100 hours, and preferably 50 to 80 hours. The reactions may be carried out in a solvent. The alkali compound is preferably added in an amount of 1.0 to 2.0 equivalents based on the amount of the hydroxyl group of Compound (1) according to the present invention wherein X is —OH. The catalyst is preferably added in an amount of 0.05 to 0.1 equivalents based on the amount of the hydroxyl group of Compound (1) according to the present invention wherein X is —OH. Y(CH$_2$)$_m$OH, glycidol, glycidyl phenyl ether, or glycidyl 4-methoxy phenyl ether is preferably added in an amount of 1.0 to 2.0 equivalents based on the amount of the hydroxyl group or Compound (1) according to the present invention wherein. X is —OH. Thereafter, the reaction mixture is, for example, washed with water and dehydrated, and purified by silica gel column chromatography to thereby obtain the target compound as a fraction.

When applying the compound of the present invention onto the surface of a magnetic disk, it is preferable to dilute the compound with a solvent before applying the compound. Examples of solvents include PF-5060, PF-5080, HFE-7100 and HFE-7200 (all manufactured by 3M) and Vertrel-XF (DuPont). The diluted compound has a concentration of 1 wt % or less, and preferably 0.001 to 0.1 wt %.

While the compound of the present invention is usable singly, the compound can also be used as mixed in a desired ratio with another material, such as Fomblin Zdol, Ztetraol, Zdol TX, AM (all manufactured by Solvay Solexis), Denmum (Daikin Industries, Ltd.), and Krytox (DuPont).

The compound of the present invention can be used as a lubricant for reducing the spacing between a magnetic disk and a head inside a magnetic disk apparatus and improving the durability against sliding. A feature of the compound of the present invention is that the hydroxyl groups at the molecular terminals can interact with the polar sites present in the carbon protective film, and the aromatic group in the molecular chain can interact with unsaturated carbon bonds present in the carbon protective film. Accordingly, the compound is usable for not only magnetic disks, but also magnetic heads, photomagnetic recording devices, and magnetic tapes, all three of which have a carbon protective film, a surface protective film, for organic materials, such as plastics, and a surface protective film for inorganic materials, such as Si$_3$N$_4$, SiC, and SiO$_2$.

FIG. 1 is a cross-sectional diagram showing a magnetic disk according to the present invention. The magnetic disk of the present invention comprises at least one recording layer 2 formed on a substrate 1, a protective layer 3 formed on the at least one recording layer 2, and a lubricant layer 4 comprising the compound of the present invention formed on the protective layer 3 as the outermost layer. Examples of substrates include aluminium alloys, ceramics such as glass, and polycarbonate.

Examples of constituent materials for a magnetic layer, which is the recording layer of the magnetic disk, include primarily elements capable of forming a ferromagnet, such as iron, cobalt, and nickel; alloys containing chromium, platinum, tantalum, or the like in addition to such elements; and oxides thereof. The layer of these materials is formed by a technique such as plating and sputtering. Examples of materials for the protective layer include SiC and SiO$_2$. The layer of these materials is formed by sputtering or CVD.

Lubricant layers presently available have a thickness of 30 Å or less. Thus, when a lubricant having a viscosity of about 100 mPa·s or more at 20° C. is applied as it is, the resulting film could have an excessively large thickness. Therefore, a lubricant dissolved in a solvent is used in coating. If the compound of the present invention is dissolved in a solvent, it is easier to desirably control the film thickness in either case where the compound of the present invention is used as a lubricant singly, or used as mixed with other lubricants. However, the concentration varies depending on the coating technique and conditions, the mixing ratio, and the like. The film thickness formed by the lubricant of the present invention is preferably 5 to 15 Å.

To facilitate the adsorption of the lubricant to the underlayer, a heat treatment and/or an ultraviolet treatment can be carried out. The heat treatment is typically carried out at a temperature of 60 to 150° C., and preferably at 80 to 150° C. The ultraviolet treatment is preferably carried out using ultraviolet rays having a dominant wavelength of 185 nm or 254 nm.

The magnetic disk of the present invention can be used in a magnetic disk apparatus comprising: a magnetic disk drive that accommodates the disk and comprises a magnetic head for recording, reproducing and erasing information and a motor for rotating the disk; and a control system for controlling the drive.

The magnetic disk according to the present invention and a magnetic disk apparatus comprising the magnetic disk can be used, for example, in external memories for electronic computers and word processors. The disk and apparatus can also be used in various devices, such as navigation systems, games, cellular phones, and PHS; internal or external recoding devices for building security, power plant administration systems, and power plant control systems; and the like.

EXAMPLES

The following Examples will describe the present invention in detail. However, the present invention is not limited to the Examples. Note that $^{19}$F-NMR was measured without a solvent, and using as the standard chemical shift a known peak that is a portion of the backbone structure of a fluoropolyether, and $^1$H-NMR was measured without a solvent and using D$_2$O as the standard substance.

Example 1

Synthesis of C$_6$H$_3$—[O—(CH$_3$)$_3$—O—CH$_2$—R—CH$_2$—OH]$_3$ (Compound 1) wherein R is —CF$_2$CF$_2$CF$_2$O(CF$_2$CF$_2$CF$_2$CF$_2$O)$_w$CF$_2$CF$_2$CF$_2$—

In an argon atmosphere, 50 g of dimethylformaldehyde, 100 g of a fluoropolyether represented by HOCH$_2$CF$_2$CF$_2$CF$_2$O(CF$_2$CF$_2$CF$_2$CF$_2$O)$_w$CH$_2$CF$_2$CF$_2$CF$_2$CH$_2$OH (w=1.5, number average molecular weight: 700, molecular weight distribution: 1.15), 25 g of triisopropylsilyl chloride, and 11 g of imidazole were mixed whale stirring at 30° C. for 12 hours. Subsequently, the mixture was washed with water, dehydrated, and purified by silica gel column chromatography, thereby giving 56 g of Compound (a1) having one hydroxyl group at one terminal and a triisopropylsilyl group at the other terminal, 56 g of Compound (a1) was dissolved in 28 g of t-butanol, and 7 g of a compound represented by formula (b1):

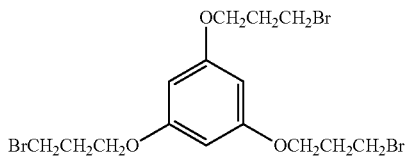

and 3 g of sodium hydride were added thereto, followed by stirring at 70° C. for 4 days.

The mixture was then washed with water, and mixed with 52 ml, of a solution of 1M tetrabutylammonium fluoride in tetrahydrofuran, followed by purification by column chromatography, thereby giving 20 g of Compound 1.

Compound 1 was a colorless transparent liquid, and had a density of 1.68 g/cm$^3$ at 20° C. Compound 1 was identified by NMR as shown below.

$^{19}$F-NMR (solvent: none, standard substance: OCF$_2$C$\underline{F}_2$CF$_2$CF$_2$O in the obtained product, which was taken as −125.8 ppm)

δ=−83.5 ppm
[30F, —OC$\underline{F}_2$CF$_2$CF$_2$C$\underline{F}_2$O—, —OC$\underline{F}_2$CF$_2$CF$_2$CH$_2$OH, (—OC$\underline{F}_2$CF$_2$CF$_2$CH$_2$OCH$_2$CH$_2$CH$_2$O)$_3$—C$_6$H$_3$], δ=−120.3 ppm
[6F, (—OCF$_2$CF$_2$C$\underline{F}_2$CH$_2$OCH$_2$CH$_2$CH$_2$O)$_3$—C$_6$H$_3$], [6F, —OCF$_2$CF$_2$C$\underline{F}_2$CH$_2$OH], δ=−123.1 ppm
[6F, —OCF$_2$CF$_2$C$\underline{F}_2$CH$_2$OH], δ=−125.8 ppm
[18F, —0CF$_2$C$\underline{F}_2$C$\underline{F}_2$CF$_2$O—], δ=−127.4 ppm
[12F, —OCF$_2$CF$_2$CF$_2$CH$_2$OH, (—OCF$_2$C$\underline{F}_2$CF$_2$CH$_2$OCH$_2$CH$_2$CH$_2$O)$_3$—C$_6$H$_3$], w=1.5

$^1$H-NMR (solvent: none, standard substance: D$_2$O)

δ=1.9 ppm
[6H, (—OCF$_2$CF$_2$CF$_2$CH$_2$OCH$_2$C$\underline{H}_2$CH$_2$O)$_3$—C$_6$H$_3$], δ=3.2 to 3.8 ppm
[27H, HOC$\underline{H}_2$CF$_2$CF$_2$CF$_2$O—, (—OCF$_2$CF$_2$CF$_2$C$\underline{H}_2$OC$\underline{H}_2$CH$_2$C$\underline{H}_2$O)$_3$—C$_6$H$_3$], δ=6.1 ppm
[3H, (—OCF$_2$CF$_2$CF$_2$CH$_2$OCH$_2$CH$_2$CH$_2$O)$_3$—C$_6$H$_3$]

Example 2

Synthesis of C$_6$H$_3$—[O—(CH$_2$)$_3$—O—CH$_2$—R—CH$_2$—OH]$_3$ (Compound 2) wherein R is —CF$_2$O(CF$_2$O)$_x$(CF$_2$CF$_2$O)$_y$CF$_2$—

In an argon atmosphere, 100 g of dimethylformaldehyde, 200 g of a fluoropolyether represented by HOCH$_2$CF$_2$O(CF$_2$O)$_x$(CF$_2$CF$_2$O)$_y$CF$_2$CH$_2$OH (x=6, y=6, number average molecular weight: 1,300, molecular weight distribution: 1.20), 25 g of triisopropylsilyl chloride, and 9 g of imidazole were mixed while stirring at 30° C. for 12 hours. Subsequently, the mixture was washed with water, dehydrated, and purified by silica gel column chromatography, thereby giving 100 g of Compound (a2) having one hydroxyl group at one terminal and a triisopropylsilyl group at the other terminal. 82 g of Compound (a2) was dissolved in 74 g of t-butanol, and 7 g of a compound represented by the above-mentioned formula (b1) and 3 g of sodium hydride were added thereto, followed by stirring at 70° C. for 4 days. The mixture was then washed with water, and mixed with 52 mL of a solution of 1M tetrabutylammonium fluoride in tetrahydrofuran, followed by purification by column chromatography, thereby giving 27 g of Compound 2.

Compound 2 was a colorless transparent liquid, and had a density of 1.76 g/cm$^3$ at 20° C. Compound 2 was identified by NMR as shown below.

$^{19}$F-NMR (solvent: none, standard substance: OC$\underline{F}_2$O in the obtained product, which was taken as −53.7 ppm)
δ=−52.1 ppm, −53.7 ppm, −55.4 ppm
[32F, —OC$\underline{F}_2$O—],
δ=−78.0 ppm, −80.0 ppm
[6F, (−OC$\underline{F}_2$CH$_2$OCH$_2$CH$_2$O)$_3$—C$_6$H$_3$],
δ=−81.0, −83.0 ppm
[6F, —C$\underline{F}_2$CH$_2$OH],
δ=−89.1 ppm, −90.7 ppm
[67F, —OC$\underline{F}_2$C$\underline{F}_2$O—]
x=5.4
y=5.6

$^1$H-NMR (solvent: none, standard substance: D$_2$O)
δ=1.9 ppm
[6H, (—OCF$_2$CH$_2$OCH$_2$C$\underline{H}_2$CH$_2$O)$_3$—C$_6$H$_3$],
δ=3.0 to 4.0 ppm
[27H, HOC$\underline{H}_2$CF$_2$O—, (—OCF$_2$C$\underline{H}_2$OC$\underline{H}_2$C$\underline{H}_2$O)$_3$—C$_6$H$_3$],
δ=6.1 ppm
[3H, (—OCF$_2$CH$_2$OCH$_2$CH$_2$O)$_3$—C$_6$H$_3$]

Example 3

Synthesis of C$_6$H$_3$—[O—(CH$_2$)$_3$—O—CH$_2$—R—CH$_2$—OH]$_3$ (Compound 3) wherein R is —CF$_2$CF$_2$O(CF$_2$CF$_2$CF$_2$O)$_z$CF$_2$CF$_2$—

In an argon atmosphere, 175 g of dimethylformaldehyde, 350 g of a fluoropolyether represented by HOCH$_2$CF$_2$CF$_2$O(CF$_2$CF$_2$CF$_2$O)$_z$CF$_2$CF$_2$CH$_2$OH (z=7, number average molecular weight: 1,480, molecular weight distribution: 1.20), 45 g of triisopropylsilyl chloride, and 18 g of imidazole were mixed while stirring at 30° C. for 12 hours. Subsequently, the mixture was washed with water, dehydrated, and purified by silica gel column chromatography, thereby giving 200 g of Compound (a3) having one hydroxyl group at one terminal and a triisopropylsilyl group at the other terminal. 140 g of Compound (a3) was dissolved in 140 g of t-butanol, and 12 g of a compound represented by the above-mentioned formula (b1) and 4 g of sodium hydride were added thereto, followed by stirring at 70° C. for 4 days. The mixture was then washed with water, and mixed with 100 mL of a solution of 1M tetrabutylammonium fluoride in tetrahydrofuran, followed by purification by column chromatography, thereby giving 30 g of Compound 3.

Compound 3 was a colorless transparent liquid, and had a density of 1.77 g/cm$^3$ at 20° C. Compound 3 was identified by NMR as shown below.

$^{19}$F-NMR (solvent: none, standard substance: OCF$_2$C$\underline{F}_2$CF$_2$O in the obtained product, which was taken as −129.7 ppm)
δ=−83.7 ppm
[88F, —OC$\underline{F}_2$C$\underline{F}_2$CF$_2$O—]
δ=−86.4 ppm
[12F, —OC$\underline{F}_2$CF$_2$CH$_2$OH, (—OC$\underline{F}_2$CF$_2$CH$_2$OCH$_2$CH$_2$O)$_3$—C$_6$H$_3$]
δ=−124.3 ppm
[6F, (—OCF$_2$C$\underline{F}_2$CH$_2$OCH$_2$CH$_2$O)$_3$—C$_6$H$_3$],
δ=−127.5 ppm
[6F, —OCF$_2$C$\underline{F}_2$CH$_2$OH],
δ=−129.7 ppm

[44F, —OCF$_2$C$\underline{F}_2$CF$_2$O—]
z=7.3

$^1$H-NMR (solvent: none, standard substance: D$_2$O)
δ=1.9 ppm
[6H, (—OCF$_2$CF$_2$CH$_2$OCH$_2$C$\underline{H}_2$CH$_2$O)$_3$—C$_6$H$_3$],
δ=2.8 to 4.2 ppm
[27H, HOC$\underline{H}_2$CF$_2$CF$_2$O—, (—OCF$_2$CF$_2$C$\underline{H}_2$OC$\underline{H}_2$C$\underline{H}_2$O)$_3$—C$_6$H$_3$]
δ=6.1 ppm
[3H, (—OCF$_2$CF$_2$CH$_2$OCH$_2$CH$_2$O)$_3$—C$_6$H$_3$]

Example 4

Synthesis of C$_6$H$_4$—[O—(CH$_2$)$_2$—O—CH$_2$—R—CH$_2$—OH]$_2$ (Compound 4) wherein R is —CF$_2$CF$_2$O(CF$_2$CF$_2$CF$_2$O)$_z$CF$_2$CF$_2$—

In an argon atmosphere, 175 g of dimethylformaldehyde, 350 g of a fluoropolyether represented by HOCH$_2$CF$_2$CF$_2$O(CF$_2$CF$_2$CF$_2$O)$_z$CF$_2$CF$_2$CH$_2$OH (z=7, number average molecular weight: 1,480, molecular weight distribution: 1.20), 45 g of triisopropylsilyl chloride, and 18 g of imidazole were mixed while stirring at 30° C. for 12 hours. Subsequently, the mixture was washed with water, dehydrated, and purified by silica gel column chromatography, thereby giving 200 g of Compound (a3) having one hydroxyl group at one terminal and a triisopropylsilyl group at the other terminal. 140 g of Compound (a3) was dissolved in 140 g of t-butanol, and 10 g of a compound represented by formula (b2):

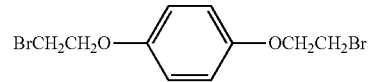

and 3 g of sodium hydride were added thereto, followed by stirring at 70° C. for 4 days.

The mixture was then washed with water, and mixed with 52 mL of a solution of 1M tetrabutylammonium fluoride in tetrahydrofuran, followed by purification by column chromatography, thereby giving 32 g of Compound 4.

Compound 4 was a colorless transparent liquid, and had a density of 1.71 g/cm$^3$ at 20° C. Compound 4 was identified by NMR as shown below.

$^{19}$F-NMR (solvent: none, standard substance: OCF$_2$C$\underline{F}_2$CF$_2$O in the obtained product, which was taken as −129.7 ppm)
δ=−83.7 ppm
[57F, —OC$\underline{F}_2$CF$_2$C$\underline{F}_2$O—]
δ=−86.4 ppm
[8F, —OC$\underline{F}_2$CF$_2$CH$_2$OH, (—OC$\underline{F}_2$CF$_2$CH$_2$OCH$_2$CH$_2$O)$_2$—C$_6$H$_4$]
δ=−124.3 ppm
[4F, (—OCF$_2$C$\underline{F}_2$CH$_2$OCH$_2$CH$_2$O)$_2$—C$_6$H$_4$]
δ=−127.5 ppm
[4F, —OCF$_2$C$\underline{F}_2$CH$_2$OH]
δ=−129.7 ppm
[28F, —OCF$_2$C$\underline{F}_2$CF$_2$O—]
z=7.1

$^1$H-NMR (solvent: none, standard substance: D$_2$O)
δ=3.2 to 3.8 ppm
[18H, HOC$\underline{H}_2$CF$_2$CF$_2$O—, (—OCF$_2$CF$_2$C$\underline{H}_2$OC$\underline{H}_2$C$\underline{H}_2$O)$_2$—C$_6$H$_4$],
δ=6.8 ppm
[4H, (—OCF$_2$CF$_2$CH$_2$OCH$_2$CH$_2$O)$_2$—C$_6$H$_4$]

Example 5

Synthesis of $C_6H_4$—[O—$(CH_2)_2$—O—$CH_2$—R—$CH_2$—$OCH_2CH(OH)CH_2OH]_2$ (Compound 5) wherein R is —$CF_2CF_2O(CF_2CF_2CF_2O)_zCF_2CF_2$—

30 g of Compound 4 obtained in Example 4 was dissolved in 15 g of t-butanol, and 1.5 g of glycidol and 0.2 g of potassium t-butoxide were added thereto, followed by stirring at 70° C. for 80 hours. Subsequently, the mixture was washed with water, and purified by column chromatography, thereby giving 13 g of Compound 5.

Compound 5 was a colorless transparent liquid, and had a density of 1.69 g/cm$^4$ at 20° C. Compound 5 was identified by NMR as shown below.

$^{19}$F-NMR (solvent: none, standard substance: $OCF_2CF_2CF_2O$ in the obtained product, which was taken as −129.7 ppm)
δ=−83.7 ppm
[55F, —$OCF_2CF_2CF_2O$—]
δ=−86.4 ppm
[8F, —$OCF_2CF_2CH_2OCH_2CH(OH)CH_2OH$, (—$OCF_2CF_2CH_2OCH_2CH_2O)_2$—$C_6H_4$]
δ=−124.3 ppm
[8F, —$OCF_2CF_2CH_2OCH_2CH(OH)CH_2OH$, (—$OCF_2CF_2CH_2OCH_2CH_2O)_2$—$C_6H_4$]
δ=−129.7 ppm
[28F, —$OCF_2CF_2CF_2O$—]
z=6.9

$^1$H-NMR (solvent: none, standard substance: $D_2O$)
δ=3.2 to 3.8 ppm
[26H, $HOCH_2CH(OH)CH_2CF_2CF_2O$—, (—$OCF_2CF_2CH_2OCH_2CH_2O)_2$—$C_6H_4$],
δ=6.8 ppm
[4H, (—$OCF_2CF_2CH_2OCH_2CH_2O)_2$—$C_6H_4$]

For comparison, Compound 6 synthesized in accordance with Example 2 of Patent Document 4 was used.
Compound 6
(HO—$CH_2$—$R^2$—$CH_2O$—$CH_2)_3$—$R^1$ wherein $R^1$ is a group represented by the following formula (a):

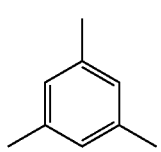

(a)

and $R^2$ is —$CF_2CF_2O(CF_2CF_2CF_2O)_zCF_2CF_2$—.

Test Example 1

Evaluation of Compound in Decomposition Resistance to Aluminium Oxide 20 wt % of $Al_2O_3$ was added to each lubricant (Compounds 1 to 6), and the mixtures were strongly shaken, followed by further mixing by ultrasound, thereby preparing samples for evaluation of decomposition resistance. Evaluation of the decomposition resistance was conducted by measuring the weight decrease of the lubricants heated at 250° C. for 100 minutes using a thermal analyzer (TG/TDA). The measurement was conducted in a nitrogen atmosphere by using 20 mg of each sample. Table 1 shows the results.

TABLE 1

| | Decrease in Weight (%) |
|---|---|
| Compound 1 | <1 |
| Compound 2 | 23 |
| Compound 3 | 5 |
| Compound 4 | 2 |
| Compound 5 | 5 |
| Compound 6 | 75 |

Test Example 2

Evaluation of Retention Properties of Lubricant on High-Speed-Rotating Disk

The lubricants (Compounds 1, 2, 5, and 6) were individually dissolved in Vertrel-XF (DuPont). These solutions contained respective lubricants in a concentration of 0.05 wt %. Magnetic disks having a diameter of 2.5 inches were individually immersed in respective solutions for 1 minute, and retrieved at a rate of 2 mm/s. Each disk was then irradiated with light having a wavelength of 185 nm for 20 seconds by using a low-pressure mercury lamp, and the average film thickness of the compound on each magnetic disk was measured with FT-IR. This film thickness is referred to as hÅ. Subsequently, the disks on which the lubricants were applied at 5,400 rpm, a temperature of 30 to 40° C., and a humidity of 80 to 90 RH % were spun at high speed for 4 weeks. Thereafter, the average film thickness of the compound remaining on each magnetic disk was measured with FT-IR. This film thickness is referred to as cÅ. To indicate the degree of adsorption of the lubricants to the magnetic disks under high-speed rotating conditions, a lubricant retention rate was determined from the following equation.

Lubricant Retention Rate (%)=100×c/h

TABLE 2

| | Initial | Week | | |
|---|---|---|---|---|
| Week | 0 | 1 | 2 | 4 |
| Compound 1 | 100.0 | 100.0 | 100.0 | 100.0 |
| Compound 2 | 100.0 | 91.2 | 93.0 | 92.7 |
| Compound 5 | 100.0 | 97.0 | 96.6 | 97.0 |
| Compound 6 | 100.0 | 86.7 | 81.8 | 74.8 |

Test Example 3

Measurement of Monomolecular Film Thickness

As described in Journal of Tribology (October 2004, Vol. 126, Page 751), the monomolecular film thickness (the thickness of one molecule) of a lubricant applied on a magnetic disk can be confirmed when the diffusive behavior of the lubricant on the disk is observed with an ellipsometer. The thickness of the terrace portion of the lubricant film is determined as the monomolecular film thickness.

Specifically, Compounds 1, 2, 3, 5, and 6 were individually dissolved in Vertrel-XF (DuPont). These solutions, respectively, contained Compounds 1, 2, 3, 5, and 6 in a concentration of 0.1 wt %. A portion (about ¼) of a magnetic disk having a diameter of 2.5 inches was immersed in each of the solutions, and retrieved at a rate of 4 mm/s, thereby preparing disks each having a portion coated with Compounds 1, 2, 3, 5, or 6, and an uncoated portion. The average film thickness of the coated portions was 32 Å.

After being prepared, these disks were placed on an ellipsometer and measured for change in the film thickness in the vicinity of the boundary of the coated portion and uncoated portion at a predetermined time interval at 50° C., whereby the monomolecular film thickness of each lubricant was determined as the film thickness of the formed terrace portion. Table 3 shows the results.

TABLE 3

| Sample | Film Thickness (Å) |
|---|---|
| Compound 1 | 10 |
| Compound 2 | 11 |
| Compound 3 | 11 |
| Compound 5 | 11 |
| Compound 6 | 13 |

The results indicate that the fluoropolyether compound having an aromatic group and hydroxyl groups according to the present invention is superior to Compound 6 having a benzene ring to which 3 fluoropolyether chains are bonded via $CH_2$ in terms of alumina decomposition resistance and lubricant retention properties, and has a smaller monomolecular film thickness than Compound 6.

DESCRIPTION OF REFERENCE NUMERALS

1 Substrate
2 Recording Layer
3 Protective Layer
4 Lubricant Layer

The invention claimed is:

1. A compound represented by formula (1):

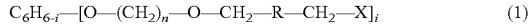  (1)

wherein n is an integer of 2 to 6; i is an integer of 2 or 3; X is a group represented by —OH, —O—$(CH_2)_m$—OH, —$OCH_2CH(OH)CH_2OH$, —$OCH_2CH(OH)CH_2O$—$C_6H_5$, or —$OCH_2CH(OH)CH_2O$—$C_6H_4$—$OCH_3$; m is an integer of 1 to 6; R is —$(CF_2)_pO(CF_2O)_x(CF_2CF_2O)_y(CF_2CF_2CF_2O)_z(CF_2CF_2CF_2CF_2O)_w(CF_2)_p$—; x and y are each a real number of 0 to 30; z is a real number of 0 to 30; w is a real number of 0 to 20; and p is an integer of 1 to 3.

2. A lubricant comprising a compound represented by formula (1):

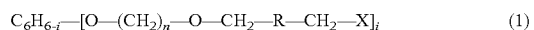  (1)

wherein n is an integer of 2 to 6; i is an integer of 2 or 3; X is a group represented by —OH, —O—$(CH_2)_m$—OH, —$OCH_2CH(OH)CH_2OH$, —$OCH_2CH(OH)CH_2O$—$C_6H_5$, or —$OCH_2CH(OH)CH_2O$—$C_6H_4$—$OCH_3$; m is an integer of 1 to 6; R is —$(CF_2)_pO(CF_2O)_x(CF_2CF_2O)_y(CF_2CF_2CF_2O)_z(CF_2CF_2CF_2CF_2O)_w(CF_2)_p$—; x and y are each a real number of 0 to 30; z is a real number of 0 to 30; w is a real number of 0 to 20; and p is an integer of 1 to 3.

3. A magnetic disk comprising, in sequence, a substrate, a recording layer, and a protective layer, the magnetic disk further comprising a lubricant layer formed on the protective layer, the lubricant layer comprising a compound represented by formula (1):

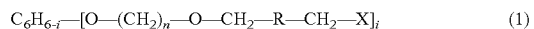  (1)

wherein n is an integer of 2 to 6; i is an integer of 2 or 3; X is a group represented by —OH, —O—$(CH_2)_m$—OH, —$OCH_2CH(OH)CH_2OH$, —$OCH_2CH(OH)CH_2O$—$C_6H_5$, or —$OCH_2CH(OH)CH_2O$—$C_6H_4$—$OCH_3$; m is an integer of 1 to 6; R is —$(CF_2)_pO(CF_2O)_x(CF_2CF_2O)_y(CF_2CF_2CF_2O)_z(CF_2CF_2CF_2CF_2O)_w(CF_2)_p$—; x and y are each a real number of 0 to 30; z is a real number of 0 to 30; w is a real number of 0 to 20; and p is an integer of 1 to 3.

* * * * *